United States Patent [19]

Glamkowski et al.

[11] Patent Number: 4,840,947
[45] Date of Patent: Jun. 20, 1989

[54] ANTIINFLAMMATORY AND ANALGESIC PIPERIDIN-4-YL-TETRACYCLIC BENZODIAZEPINES AND USE THEREAS

[75] Inventors: Edward J. Glamkowski, Warren; Yulin Chiang, Convent Station, both of N.J.; Frederick J. Ehrgott, Jr., Norwich, Conn.

[73] Assignee: Hoechst-Roussel Pharmaceuticals, Inc., Somerville, N.J.

[21] Appl. No.: 918,242

[22] Filed: Oct. 14, 1986

[51] Int. Cl.[4] .................... C07D 487/04; A61K 31/55
[52] U.S. Cl. ..................................... 514/219; 540/555
[58] Field of Search ........................ 540/555; 514/219

[56] References Cited

U.S. PATENT DOCUMENTS 4,186,199  1/1980  Glomowski et al. ............ 424/232

Primary Examiner—David B. Springer
Attorney, Agent, or Firm—Tatsuya Ikeda

[57] ABSTRACT

There are disclosed compounds of the formula

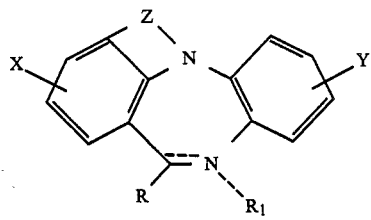

where X and Y are independently hydrogen, loweralkyl, halogen or trifluoromethyl; Z is $-CH_2CH_2-$, $-CH=CH-$ or $-CH_2CH_2CH_2-$; R is

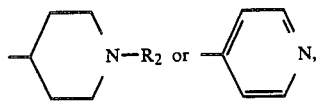

$R_2$ being hydrogen, loweralkyl, ethoxycarbonyl, 2,2,2-trichloroethoxycarbonyl or phenoxycarbonyl; and $R_1$ is hydrogen, loweralkanoyl, loweralkyl, ethoxycarbonyl, 2,2,2-trichloroethoxycarbonyl or phenoxycarbonyl; the dotted line within the seven-membered ring and the dotted line between $R_1$ and the ring nitrogen being optional bonds such that the former is absent and the latter present when R is

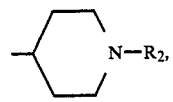

whereas the former is present and the latter absent when R is

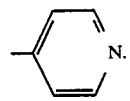

These compounds display antiinflammatory activities and analgesic activities.

20 Claims, No Drawings

ANTIINFLAMMATORY AND ANALGESIC PIPERIDIN-4-YL-TETRACYCLIC BENZODIAZEPINES AND USE THEREAS

The present invention relates to compounds of the formula

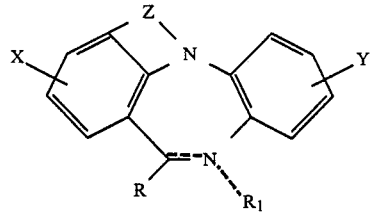

where X and Y are independently hydrogen, loweralkyl, trifluoromethyl or halogen; Z is —CH$_2$CH$_2$—, —CH=CH— or —CH$_2$CH$_2$CH$_2$—; R is

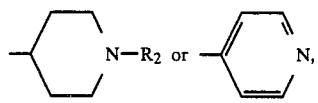

R$_2$ being hydrogen, loweralkyl, ethoxycarbonyl, 2,2,2-trichloroethoxycarbonyl or phenoxycarbonyl; and R$_1$ is hydrogen, loweralkanoyl, loweralkyl, ethoxycarbonyl, 2,2,2-trichloroethoxycarbonyl or phenoxycarbonyl; the dotted line within the seven-membered ring and the dotted line between R$_1$ and the ring nitrogen being optional bonds such that the former is absent and the latter present when R is

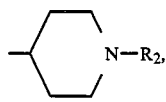

whereas the former is present and the latter absent when R is

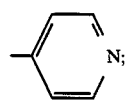

which display antiinflammatory and analgesic activities, pharmaceutical compositions comprising these compounds and a method of alleviating inflammation and/or pain by use of these compounds.

Unless otherwise stated or indicated, the following definitions shall apply throughout the specification and the appended claims.

Unless otherwise stated or indicated, the term loweralkyl denotes a straight or branched alkyl group having from 1 to 6 carbon atoms. Examples of said loweralkyl group include methyl, ethyl, n-propyl, iso-propyl, n-butyl, iso-butyl, sec-butyl, t-butyl and straight- and branched-chain pentyl and hexyl.

Unless otherwise stated or indicated, the term halogen shall mean fluorine, chlorine, bromine or iodine.

The term loweralkanoyl shall men a group obtained by removing a hydroxy group from the carboxyl group of a loweralkanoic acid, and thus it includes for instance formyl, acetyl and the like.

It should be noted that an asymmetric center exists at the ring carbon carrying the R group in Formula I when the optional bond within the seven-membered ring is absent. Throughout the specification and appended claims, a given chemical structure, formula or name shall encompass all optical isomers including racemic mixture.

The compounds of this invention are prepared by following one or more of the steps described below. Throughout the description of the synthetic steps, the definitions of X, Y, Z, R, R$_1$ and R$_2$ are as given above unless otherwise stated or indicated, and other nomenclatures used below shall have the definitions given at their respective first appearances unless otherwise stated or indicated.

STEP A

A compound of formula II where Z' is —CH$_2$CH$_2$— or —CH$_2$CH$_2$CH$_2$— is cyclized in the presence of POCl$_3$ to afford a compound of formula III.

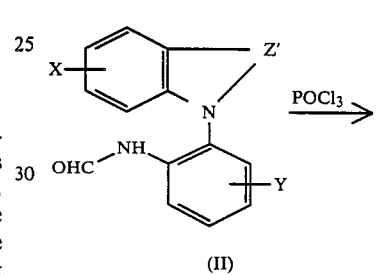

Said cyclization is conducted typically by refluxing compound II in phosphorus oxychloride for a few hours.

A reaction scheme for preparing the starting compound II where Z' is —CH$_2$CH$_2$— is described, for instance, in E. Glamkowski and J. Fortunato, J. Heterocyclic Chem., 16, 865–869 (1979). Substantially the same reaction scheme can be used for preparing the compound II where Z' is —CH$_2$CH$_2$CH$_2$—.

STEP B

A compound of formula IV is reacted with isonicotinyl chloride to afford a compound of formula V.

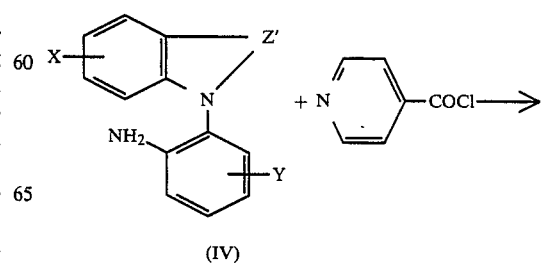

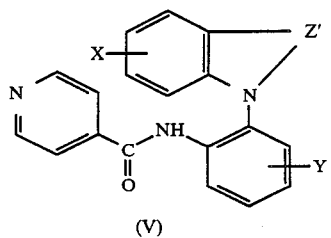

(V)

Said reaction is typically conducted in the presence of an acid scavenger such as triethylamine and a suitable solvent such as chloroform and stirring the reaction mixture at room temperature for a few hours.

STEP C

Compound V is cyclized in the presence of POCl$_3$ in substantially the same manner as in STEP A to afford a compound of formula VI.

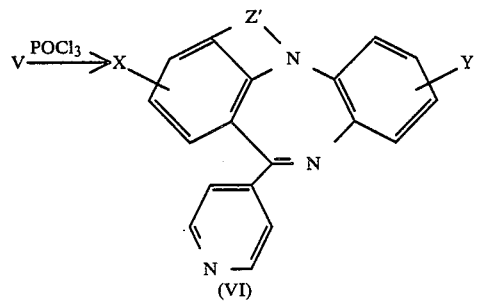

(VI)

STEP D

A compound of formula VII where R$_3$ is hydrogen or 4-pyridinyl which is obtained from STEP A or STEP C is dehydrogenated to afford a compound of formula VIII.

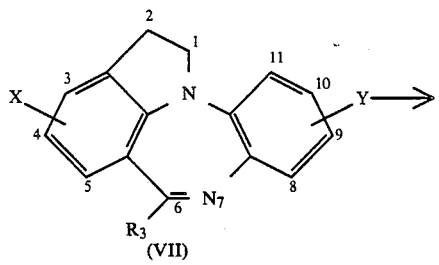

(VII)

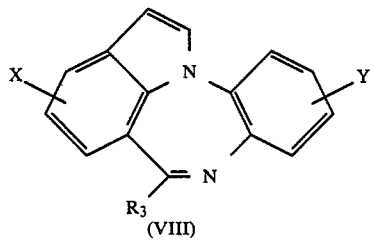

(VIII)

Said dehydrogenation is conducted typically in the presence of 2,3-dichloro-5,6-dicyano-1,4-benzoquinone and a suitable solvent such as toluene and refluxing the reaction mixture under an inert atmosphere for a few hours.

STEP E

A compound of formula IX prepared in STEP A or D is reacted with a Grignard reagent of formula X where R$_4$ is loweralkyl to afford a compound of formula XI.

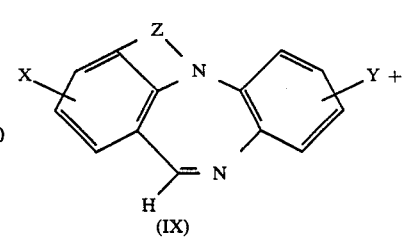

(IX)

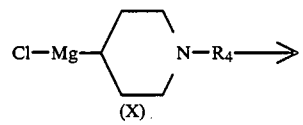

(X)

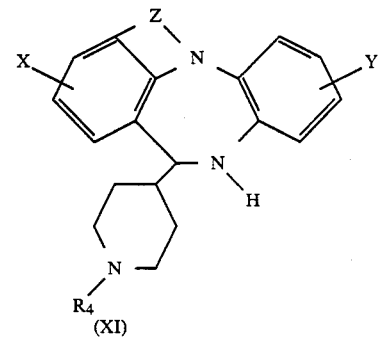

(XI)

The Grignard reagent X is prepared from magnesium and a compound of the formula

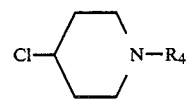

typically in a suitable medium such as anhydrous tetrahydrofuran and in the presence of 1-bromo-2-chloroethane or 1,2-dibromoethane which facilitates the initiation of the Grignard reaction. Usually, the reaction mixture is heated at reflux under an inert gas atmosphere for about an hour and thereafter cooled to below room temperature. The reaction between compound IX and the Grignard reagent X is conducted typically by adding the mixture obtained above to a stirred ice cold mixture consisting of compound IX and anhydrous tetrahydrofuran and further stirring the resultant mixture for a short period of time such as less than one hour.

STEP F

Compound XI is reacted with a compound of the formula R$_5$COCl where R$_5$ is loweralkyl to afford a compound of formula XII below.

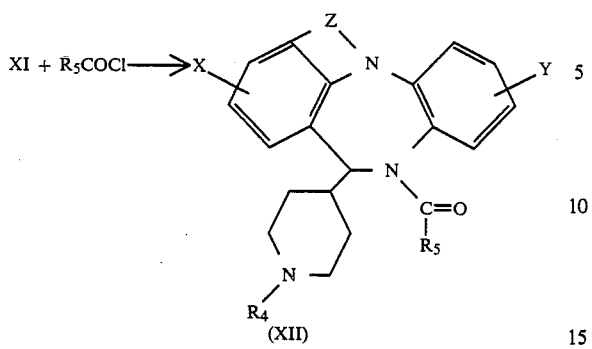

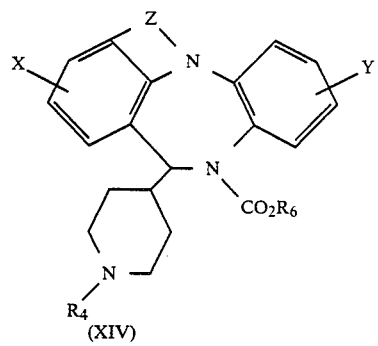

The above reaction is conducted typically in the presence of an acid scavenger such as sodium bicarbonate and a suitable medium such as anhydrous chloroform and stirring the reaction mixture at room temperature for a few hours or less.

STEP G

Compound XI is reacted with formic-acetic mixed anhydride to afford a compound of formula XIII.

The above reaction is typically conducted in the presence of a suitable medium such as chloroform and an acid scavenger such as sodium bicarbonate and stirring the reaction mixture at room temperature overnight.

STEP I

A compound of formula XV where $R_7$ is hydrogen or loweralkyl which is obtained from STEP F or G is reduced with borane to afford a compound of formula XVI.

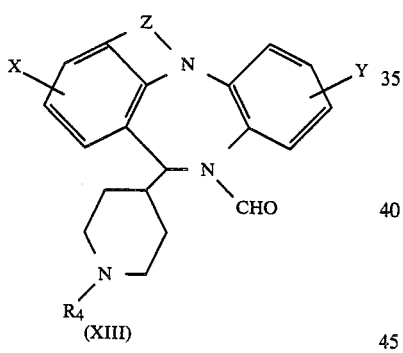

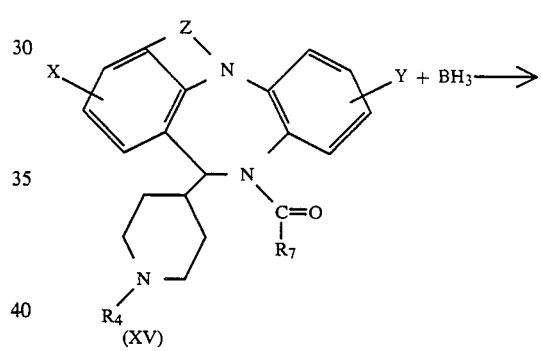

The above reaction is conducted typically by first preparing formic-acetic mixed anhydride from acetic anhydride and formic acid and then adding the mixed anhydride to a solution of compound XI in a suitable solvent such as chloroform and stirring the resultant mixture at room temperature for a short period of time such as one hour or less.

STEP H

Compound XI is reacted with ethyl chloroformate, 2,2,2-trichloroethyl chloroformate or phenyl chloroformate (written as $ClCO_2R_6$ where $R_6$ is $CH_2CH_3$, $CH_2CCl_3$ or $C_6H_5$) to afford a compound of formula XIV.

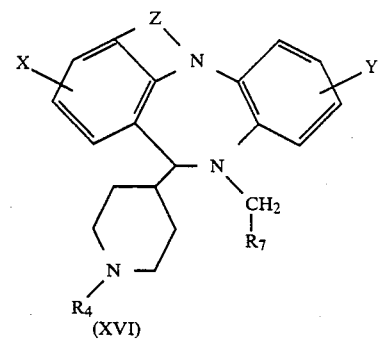

The above reduction is conducted typically by adding a solution of borane-dimethylsulfide complex in a suitable solvent such as tetrahydrofuran to a solution of compound XV in the same solvent and stirring the mixture at room temperature for a few hours and thereafter at reflux for less than one hour.

STEP J

A compound of formula XVII where $R_1$ is not hydrogen which is obtained from one of the foregoing STEPS is reacted with a chloroformate of the formula $ClCO_2R_6$ to afford a compound of formula XVIII.

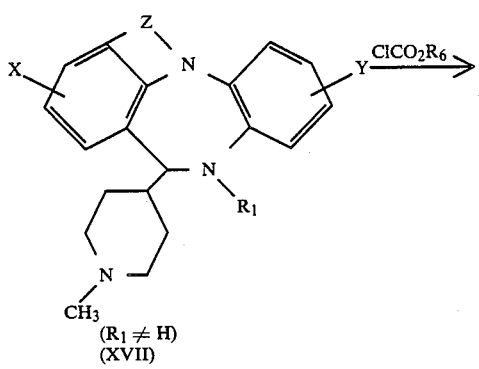

(R₁ ≠ H)
(XVII)

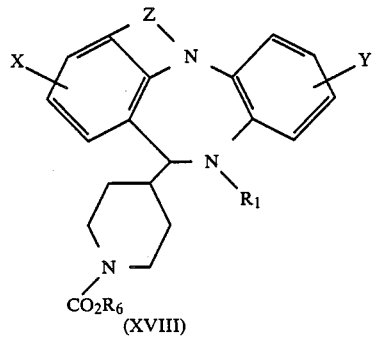

(XVIII)

The above reaction is typically conducted in the presence of an acid scavenger such as sodium or potassium bicarbonate and a suitable medium such as benzene and refluxing the reaction mixture for about a day.

STEP K

A compound of formula XVII (where $R_1$ may be hydrogen) is reacted with alpha-chloroethyl chloroformate and the resultant carbamate (when $R_1$ is not hydrogen) or bis-carbamate (when $R_1$ is hydrogen) product is cleaved with methanol under a mild condition to afford a demethylated compound of formula XIX as a hydrochloride salt.

XVII + CH₃CHClOCOCl $\xrightarrow{CH_3OH}$

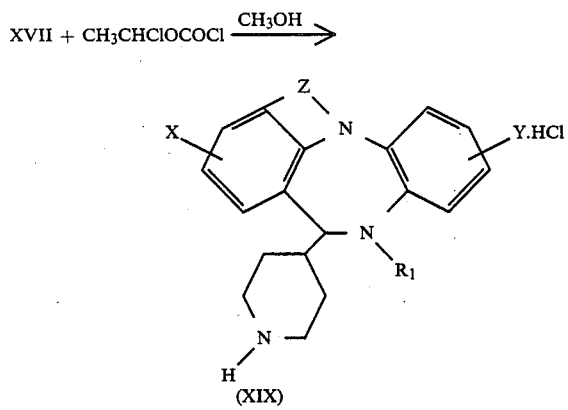

(XIX)

The first step, namely, the carbamate or bis-carbamate formation is conducted typically in a suitable solvent such as 1,2-dichloroethane and gently refluxing the reaction mixture for a few hours. The carbamate or bis-carbamate product can be isolated by a routine procedure, but for the purpose of obtaining the demethylated compound, removal of the solvent from the above reaction mixture by evaporation is sufficient. The second step, namely, the cleavage of the carbamate or bis-carbamate with methanol is conducted under a mild condition, for instance, by passing the carbamate or bis-carbamate through a flash chromatographic column at room temperature with a suitable methanol-containing solvent being used as an eluent, or by warming a mixture of the carbamate or bis-carbamate and methanol at about 50° C. for about one hour. A discussion of N-dealkylation of tertiary amines using alpha-chloroethyl chloroformate is presented in R. A. Olofson et al., J. Org. Chem. 1984, 49, 2081-2082.

The compounds of the present invention are useful as antiinflammatory agents due to their ability to suppress inflammation in mammals. The activity of the compounds is demonstrated in the carrageenin induced rat paw edema antiinflammatory assay [Proc. Soc. Exptl. Biol. Med., III 544 (1962), and J. Pharmacol. Exp., 141 (1963)]. The results of the antiinflammatory test of some of the compounds of this invention are given in Table I along with the result of a standard compound.

TABLE 1

| Inhibition of Carrageenan-Induced Rat Paw Edema | |
|---|---|
| Compound | Percent Inhibition |
| 6-(1-methylpiperidin-4-yl)-1,2,6,7-tetrahydrobenzo[b]-pyrrolo[3,2,1-jk][1,4]-benzodiazepine fumarate ethanolate | $ED_{50}$ = 41.5 mg/kg, p.o. |
| 6-(1-methylpiperidin-4-yl)-1,2,6,7-tetrahydrobenzo[b]-pyrrolo[3,2,1-jk][1,4]-benzodiazepine-7-carboxylic acid, 2,2,2-trichloroethyl ester | 44% at 100 mg/kg, p.o. |
| 9-bromo-6-(1-methylpiperidin-4-yl)-1,2,6,7-tetrahydrobenzo[b]-pyrrolo[3,2,1-jk][1,4]benzodiazepine | 40% at 100 mg/kg, p.o. |
| 7-(1-methyl-4-piperidinyl)-2,3,7,8-tetrahydro-1H—quino[1,8-ab][1,5]-benzodiazepine hemifumarate hemihydrate (prior art compound) | 21% at 100 mg/kg, p.o. |
| Phenylbutazone | $ED_{50}$ = 50 mg/kg, p.o. |

The antiinflammatory activities of the compounds of the present invention are also demonstrated in the adjuvant-induced polyarthritis syndrome in rats. This activity was measured by a procedure similar to that described by C. M. Pearson and F. D. Wood, Arthritis and Rheumatism, 2, 440 (1959).

Groups of 10 male Charles River-Wistar Lewis rats weighing 150 to 175 g were individually housed and maintained on a regular rat chow diet. Water was given ad libitum. The adjuvant was prepared by suspending 75 mg of *Mycobacterium butyricum* (Difco Laboratories, Detroit, Mich.) in 10 ml of white paraffin oil with continuous stirring for 2 hours at room temperature prior to administration. Test compounds are prepared by suspending the drug in water, adding one drop of Tween 80 per 10 ml of suspension, and homogenizing. The adjuvant suspension (0.1 ml) was injected into the footpad of the left hind paw of the rat. Test compound suspensions were administered orally (10 ml/kg) the day before adjuvant suspension injection and the administration was continued for 21 days. One group of ten rats was used for the test drug. Standard, adjuvant-injected control and non-injected control groups are run along with the test drug. Control animals received vehicle (10 ml/kg). Three doses of test drug and one dose of standard preparation were used. Injected and non-injected paw volumes were determined on the day the adjuvant suspension was given, and on subsequent days thereafter (usually days 5, 10, 18, and 21) by the method of C. A. Winter, et al., Proc. Soc. Exp. Biol. Med., 111, 544 (1962).

The percent inhibition of paw volume (injected and non-injected hind paw) was calculated by the following formula:

$$\% \text{ Inhibition} = \frac{\text{Mean Paw Volume Change of Injected (or Non-injected) Control} - \text{Mean Paw Volume Change of Drug Treated}}{\text{Mean Paw Volume Change of Injected (or Non-Injected) Control}} \times 100$$

$ED_{50}$-values, i.e., the dose at which the drug affects a 50% inhibition of paw volume, were estimated by the method of J. T. Litchfield and F. Wilcoxon, J. Pharm. Exp. Ther., 96, 99 (1948) and statistically evaluated by means of the student "t" test. The test results of some of the compounds of the present invention are presented in Table 2 along with the results of a standard compound.

TABLE 2

| Adjuvant-Induced Polyarthritis In Rats | | |
|---|---|---|
| Compound | Adjuvant-treated paw | Non-Injected paw |
| 6-(1-methylpiperidin-4-yl)-1,2,6,7-tetrahydrobenzo[b]pyrrolo[3,2,1-jk]-[1,4]benzodiazepine fumarate ethanolate | $ED_{50}$ = 73.6 mg/kg, p.o. | $ED_{50}$ = 18.5 mg/kg, p.o. |
| 9-bromo-6-(1-methyl-piperidin-4-yl)-1,2,6,7-tetrahydrobenzo[b]pyrrolo-[3,2,1-jk][1,4]benzodiazepine | $ED_{50}$ = 112 mg/kg, p.o. | $ED_{50}$ = 3.6 mg/kg, p.o. |
| 9-fluoro-6-(1-methyl-piperidin-4-yl)-1,2,6,7-tetrahydrobenzo[b]pyrrolo-[3,2,1-jk][1,4]benzodiazepine | 48% at 50 mg/kg, p.o. | 116% at 50 mg/kg, p.o. |
| 7-(1-methyl-4-piperidinyl)-2,3,7,8-tetrahydro-1H—quino[1,8-ab][1,5]-benzodiazepine hemifumarate hemihydrate (prior art compound) | 39% at 50 mg/kg, p.o. | 79% at 50 mg/kg, p.o. |
| Phenylbutazone | $ED_{50}$ = 14 mg/kg, p.o. | $ED_{50}$ = 9.4 mg/kg, p.o. |

The compounds of the present invention are also useful as analgesic agents due to their ability to alleviate pain in mammals. The activity of the compounds is demonstrated in the 2-phenyl-1,4-benzoquinone induced writhing test in mice, a standard assay for analgesia [Proc. Soc. Exptl. Biol. Med., 95, 729 (1957)]. Table 3 shows the test results of some of the compounds of this invention along with the result of a standard compound.

TABLE 3

| Phenylquinone Induced Writhing in Mice | |
|---|---|
| Compound | Percent Inhibition |
| 6-(1-methylpiperidin-4-yl)-1,2,6,7-tetrahydrobenzo[b]pyrrolo[3,2,1-jk]-[1,4]benzodiazepine fumarate ethanolate | 51% at 20 mg/kg, s.c. |
| 9-fluoro-6-(1-methylpiperidin-4-yl)-1,2,6,7-tetrahydrobenzo[b]pyrrolo-[3,2,1-jk][1,4]benzodiazepine | 35% at 20 mg/kg, s.c. |
| 4-bromo-6-(1-methylpiperidin-4-yl)-1,2,6,7-tetrahydrobenzo[b]pyrrolo-[3,2,1-jk][1,4]benzodiazepine ethanolate | 47% at 20 mg/kg, s.c. |
| 7-formyl-6-(1-methylpiperidin-4-yl)-1,2,6,7-tetrahydrobenzo[b]-pyrrolo[3,2,1-jk][1,4]benzodiazepine formate | $ED_{50}$ = 0.9 mg/kg, s.c. |
| 7-(1-methyl-4-piperidinyl)-2,3,7,8-tetrahydro-1H—quino[1,8-ab][1,5]-benzodiazepine hemifumarate hemihydrate | 27% at 20 mg/kg, s.c. |
| 7-methyl-6-(1-methylpiperidin-4-yl)-1,2,6,7-tetrahydrobenzo[b]-pyrrolo[3,2,1-jk][1,4]benzodiazepine (prior art compound) | $ED_{50}$ = 2.6 mg/kg, s.c. |
| Propoxyphene | $ED_{50}$ = 3.9 mg/kg, s.c. |

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purposes of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such composition is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, coatings. Thus tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of active compounds, but may be varied depending upon the particular form and may conveniently be between 4% and about 70% of the weight of the unit. The amount of active compound in such compositions is such that a suitable dosage will be obtained. Preferred compositions and preparations according to the present invention are prepared so that a parenteral dosage unit contains between 0.5 to 100 milligrams of active compounds.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of this invention include:
6-(1-methylpiperidin-4-yl)-1,2,6,7-tetrahydrobenzo[b]pyrrolo[3,2,1-jk][1,4]benzodiazepine;
4-bromo-6-(1-methylpiperidin-4-yl)-1,2,6,7-tetrahydrobenzo[b]pyrrolo[3,2,1-jk][1,4]benzodiazepine;
9-bromo-6-(1-methylpiperidin-4-yl)-1,2,6,7-tetrahydrobenzo[b]pyrrolo[3,2,1-jk][1,4]benzodiazepine;
9-bromo-6-(1-methylpiperidin-4-yl)-6,7-dihydrobenzo[b]pyrrolo[3,2,1-jk][1,4]benzodiazepine;
4,9-dibromo-6-(1-methylpiperidin-4-yl)-1,2,6,7-tetrahydrobenzo[b]pyrrolo[3,2,1-jk][1,4]benzodiazepine;
9-fluoro-6-(1-methylpiperidin-4-yl)-1,2,6,7-tetrahydrobenzo[b]pyrrolo[3,2,1-jk][1,4]benzodiazepine;
9-methyl-1,2-dihydrobenzo[b]pyrrolo[3,2,1-jk][1,4]benzodiazepine;
9-methyl-6-(1-methylpiperidin-4-yl)-1,2,6,7-tetrahydrobenzo[b]pyrrolo[3,2,1-jk][1,4]benzodiazepine;
9-trifluoromethyl-6-(1-methylpiperidin-4-yl)-1,2,6,7-tetrahydrobenzo[b]pyrrolo[3,2,1-jk][1,4]benzodiazepine;
6-(piperidin-4-yl)-1,2,6,7-tetrahydrobenzo[b]pyrrolo[3,2,1-jk][1,4]benzodiazepine;
6-(1-methylpiperidin-4-yl)-1,2,6,7-tetrahydrobenzo[b]pyrrolo[3,2,1-jk][1,4]benzodiazepine-7-carboxylic acid, 2,2,2-trichloroethyl ester;
6-[1-(2,2,2-trichloroethoxycarbonyl)-piperidin-4-yl]-1,2,6,7-tetrahydrobenzo[b]pyrrolo[3,2,1-jk][1,4]benzodiazepine-7-carboxylic acid, 2,2,2-trichloroethyl ester;
7-formyl-6-(1-methylpiperidin-4-yl)-1,2,6,7-tetrahydrobenzo[b]pyrrolo[3,2,1-jk][1,4]benzodiazepine;
7-methyl-6-(1-methylpiperidin-4-yl)-1,2,6,7-tetrahydrobenzo[b]pyrrolo[3,2,1-jk][1,4]benzodiazepine;
6-(4-pyridinyl)-1,2-dihydrobenzo[b]pyrrolo[3,2,1-jk][1,4]benzodiazepine; and
7-(1-methyl-4-piperidinyl)-2,3,7,8-tetrahydro-1H-quino[1,8-ab][1,5]benzodiazepine, including the racemates and the + and − optical isomers of the above compounds.

The following examples are given for the purpose of illustrating this invention:

EXAMPLE 1

6-(1-Methylpiperidin-4-yl)-1,2,6,7-tetrahydrobenzo[b]pyrrolo[3,2,1-jk][1,4]benzodiazepine fumarate ethanolate To 11.38 g of magnesium turnings in 50 ml of tetrahydrofuran was added approximately 1 ml of 1,2-dibromoethane and a Grignard reaction was initiated by heating the mixture. About half of a solution prepared from 31.27 g of 4-chloro-N-methyl-piperidine and 200 ml of tetrahydrofuran was added to the refluxing, initiated Grignard mixture. Seeding with iodine and further reflux produced an appearance characteristic of successful Grignard formation. After addition of the other half of the solution and 1.5 hours of further reflux, the mixture was allowed to cool to 45° C. and a solution of 17.18 g of 1,2-dihydrobenzo[b]pyrrolo[3,2,1-jk][1,4]benzodiazepine in 300 ml of tetrahydrofuran was added over a 15 minute period. After refluxing this mixture for 30 minutes, the mixture was stirred at room temperature for a time. The liquid phase was then decanted from the unreacted magnesium into a stirred mixture of 105 ml of concentrated hydrochloric acid and 1.25 kg of crushed ice. This mixture was then made basic by addition of 150 ml of concentrated ammonium hydroxide solution and extracted with ethyl acetate (1×500 ml, 1×250 ml). The combined ethyl acetate extracts were washed with water (2×250 ml) and saturated sodium chloride solution (250 ml) and dried over anhydrous sodium sulfate. Filtration and concentration in vacuo afforded a foam weighing 24.9 g. This material was purified by flash chromatography on 500 g of silica gel using dichloromethane as a solvent initially, followed by 5% and then 10% methanol/dichloromethane solution. This procedure afforded 11.5 g of foam, which was dissolved in 250 ml of absolute ethanol and treated with a solution prepared from 4.39 g of fumaric acid and 250 ml of absolute ethanol. Within a few minutes a precipitate formed in the stirred mixture. After one hour of stirring, the solid was filtered off, washed successively with ethanol and ether and dried in vacuo to afford 10.59 g of crystalline solid, m.p. 197°–200° C., melts with bubbling. Recrystallization of this material twice from absolute ethanol afforded 6.3 g of crystalline solid, m.p. 204°–206.5° C. with bubbling.

ANALYSIS: Calculated for $C_{21}H_{25}N_3 \cdot C_4H_4O_4 \cdot C_2H_5OH$: 67.34%C, 7.33%H, 8.73%N, Found: 66.97%C, 7.47%H, 8.78%N.

EXAMPLE 2

4-Bromo-6-(1-methylpiperidin-4-yl)-1,2,6,7-tetrahydrobenzo[b]pyrrolo[3,2,1-jk][1,4]benzodiazepine ethanolate In a 1 L dried three-necked flask, 1,2-dibromoethane (0.5 ml) was added to a refluxing slurry of magnesium chips (9.0 gm) in tetrahydrofuran (70 ml) to initiate a Grignard reaction. A solution of N-methyl-4-chloropiperidine (30 ml) in tetrahydrofuran (30 ml) was added in portions to maintain a fast refluxing over a period of 10 minutes. The resultant slurry was refluxed for 1.5 hours, during which the mixture turned milky white. The mixture was cooled to 0° C. with an ice-water bath. A solution of 4-bromo-1,2-dihydrobenzo[b]pyrrolo[3,2,1-jk][1,4]benzodiazepine (15 gm) in tetrahydrofuran (100 ml) was added in 5 minutes. The mixture was stirred for 1 hour.

The mixture was diluted with ethyl acetate (800 ml) and quenched with 1 L of saturated ammonium chloride solution. The ethyl acetate phase was separated and the ammonium chloride solution was basified with ammonium hydroxide to pH=10 and extracted twice with ethyl acetate (2×200 ml). The combined ethyl acetate extracts were washed with water (2×800 ml) and brine (1 L) and dried over anhydrous magnesium sulfate. The solution was filtered and concentrated to an oil-foam product (about 19 gm).

The product was purified by flash chromatography over silica (200 gm, eluted with 2% methanol/dichloromethane, 4 L; 2.5% methanol/dichloromethane, 2 L; 3% methanol/dichloromethane, 2 L). The purified product (10 gm) was recrystallized from ethanol (60 ml) to give 6.2 gm of crystalline powder, m.p. 207°–209° C.

ANALYSIS: Calculated for $C_{21}H_{24}BrN_3 \cdot C_2H_5OH$: 62.15%C, 6.80%H, 9.45%N, Found: 62.24%C, 6.85%H, 9.42%N.

EXAMPLE 3

9-Bromo-6-(1-methylpiperidin-4-yl)-1,2,6,7-tetrahydrobenzo[b]pyrrolo[3,2,1-jk][1,4]benzodiazepine 1,2-Dibromoethane (0.5 ml) was added to a refluxing slurry of magnesium chips (12 gm) in tetrahydrofuran (60 ml) to initiate a Grignard reaction. N-Methyl-4-chloropiperidine (55 ml) in tetrahydrofuran (100 ml) was added rapidly. The mixture was refluxed for 1 hour, during which a white precipitate formed. A solution of 9-bromo-1,2-dihydrobenzo[b]pyrrolo[3,2,1-jk][1,4]benzodiazepine (30 gm) in tetrahydrofuran (150 ml) was added at 0° C. After one hour of stirring, the mixture was poured into cold saturated ammonium chloride solution (750 ml) and extracted with ethyl acetate (2×400 ml). The ammonium chloride solution was basified with ammonium hydroxide and extracted once with ethyl acetate (400 ml). The combined ethyl acetate solutions were washed with brine (2×500 ml), dried over anhydrous magnesium sulfate and concentrated to a solid (38 gm). The crude solid was purified by flash chromatography (700 gm silica, eluted with 4% methanol/dichloromethane, 6 L; 4% methanol/0.5% ammonium hydroxide/dichloromethane, 4 L). The fractions containing the desired product were pooled and concentrated to give 23 gm of a solid. Recrystallization from dichloromethane/ethanol (200 ml:1 L) yielded 17.0 gm of crystals, m.p. 206°–208° C.

ANALYSIS: Calculated for $C_{21}H_{24}BrN_3$: 63.62%C, 6.07%H, 10.55%N, Found: 63.14%C, 6.18%H, 10.38%N.

EXAMPLE 4

4,9-Dibromo-6-(1-methylpiperidin-4-yl)-1,2,6,7-tetrahydrobenzo[b]pyrrolo[3,2,1-jk][1,4]benzodiazepine 1,2-Dibromoethane (0.5 ml) was added to a refluxing slurry of magnesium chips (6 gm) in tetrahydrofuran (70 ml) to initiate a Grignard reaction. A solution of N-methyl-4-chloropiperidine (35 ml) in tetrahydrofuran (100 ml) was added rapidly. The reaction mixture was refluxed for 2 hours, during which a white precipitate formed. The mixture was cooled to room temperature and transferred to a flask containing 4,9-dibromo-1,2-dihydrobenzo[b]pyrrolo[3,2,1-jk][1,4]benzodiazepine (20 gm) in tetrahydrofuran (200 ml) in one portion at ice-temperature. After 1 hour of stirring, the mixture was poured into ice-water/concentrated hydrochloric acid (600 ml:35 ml), and stirred for 15 minutes. The acid solution was slowly added to a stirred mixture prepared from dichloromethane (1 L) and an ammonium hydroxide solution (40 ml). The organic solution was separated, washed with water (500 ml) and brine (2×500 ml) and dried over anhydrous magnesium sulfate. The solution was filtered and concentrated to an oil (26 gm).

The crude product was purified on a silica gel column (400 gm, eluted with 4% methanol/dichloromethane). The resultant product (14.8 gm) was recrystallized from ethanol (450 ml) to yield 9.5 gm of crystals, m.p. 237°–238° C.

ANALYSIS: Calculated for $C_{21}H_{23}Br_2N_3$: 52.85%C, 4.86%H, 8.80%N, Found: 52.52%C, 4.72%H, 8.86%N.

EXAMPLE 5

9-Fluoro-6-(1-methylpiperidin-4-yl)-1,2,6,7-tetrahydrobenzo[b]pyrrolo[3,2,1-jk][1,4]benzodiazepine In a dried 1 L three-necked flask, 1,2-dibromoethane (0.5 ml) was added to a refluxing slurry of magnesium chips (6.3 gm) in tetrahydrofuran (50 ml) to initiate a Grignard reaction. The mixture became cloudy and a vigorous reaction ensued. A solution of N-methyl-4-chloropiperidine (37 ml) in tetrahydrofuran (40 ml) was added in portions to maintain a fast reflux over a period of 10 minutes. The resultant slurry was refluxed for 1.5 hours and thereafter cooled to about 5° C. with an ice-water bath. A solution of 9-fluoro-1,2-dihydrobenzo[b]pyrrolo[3,2,1-jk][1,4]benzodiazepine (15.7 gm) in tetrahydrofuran (70 ml) was added in 5 minutes. The mixture was stirred for 40 minutes.

The mixture was diluted with ethyl acetate (1 L) and washed with saturated ammonium chloride solution (700 ml). The organic phase was separated and the aqueous phase was basified with ammonium hydroxide and extracted twice with ethyl acetate (2×200 ml). The combined ethyl acetate solution was washed with water (2×500 ml) and brine (2×500 ml), and dried over anhydrous magnesium sulfate. The solution was filtered and concentrated to a foam-oil product.

The product was purified by flash chromatography over silica (370 gm, eluted with 4% methanol/dichloromethane, 4 L) to afford 13.5 gm of a solid. Recrystallization from acetone (65 ml) provided 6.23 gm of crystals, m.p. 192°–194° C.

ANALYSIS: Calculated for $C_{21}H_{24}FN_3$: 74.75%C, 7.17%H, 12.45%N, Found: 74.65%C, 7.18%H, 12.44%N.

EXAMPLE 6

9-methyl-1,2-dihydrobenzo[b]pyrrolo[3,2,1-jk][1,4]benzodiazepine 1-(2-Formamido-4-methylphenyl)indoline (34 gm) in phosphorous oxychloride (220 ml) was heated at 100° C. (steam bath) for 2.5 hours, during which the product precipitated. The mixture was cooled to room temperature and ether (400 ml) was added and the excess phosphorous oxychloride was removed by filtration. The solids were washed with ether (3×400 ml) and thereafter dissolved in a mixed solvent of 10% triethylamine/dichloromethane (1.2 L). The organic solution was washed with 10% sodium hydroxide solution (350 ml), water (400 ml) and brine (600 ml), and dried over anhydrous magnesium sulfate. The solvent was removed under reduced pressure to leave an oil (28 gm). The oil was purified by flash chromatography over silica gel (320 gm, eluted with dichloromethane, 6 L). The resultant oil turned into crystals on shaking with ether (150 ml). The crystals were collected and dried to afford 25.9 gm, m.p. 77°–78° C.

ANALYSIS: Calculated for $C_{16}H_{14}N_2$: 82.02%C, 6.22%H, 11.96%N, Found: 82.29%C, 5.99%H, 11.71%N.

EXAMPLE 7

9-Methyl-6-(1-methylpiperidin-4-yl)-1,2,6,7-tetrahydrobenzo[b]pyrrolo[3,2,1-jk][1,4]benzodiazepine In a 1 L three-necked flask, 1,2-dibromoethane (0.3 ml) was added to a refluxing slurry of magnesium chips (4.1 gm) in tetrahydrofuran (80 ml) to initiate a Grignard reaction. A solution of N-methyl-4-chloropiperidine (28 ml) in tetrahydrofuran (30 ml) was added in portions to maintain a fast reflux. The resultant slurry was refluxed for 1 hour and cooled to about 0° C. A solution of 9-methyl-1,2-dihydrobenzo[b]pyrrolo[3,2,1-jk][1,4]benzodiazepine (10.0 gm) in tetrahydrofuran (50 ml) was added dropwise. After 1.5 hours of stirring, the mixture was diluted with ethyl acetate (400 ml) and with saturated ammonium chloride solution (600 ml). The organic phase was separated. The aqueous phase was basified with 50% sodium hydroxide solution and then it was extracted twice with ethyl acetate (400 ml). The combined ethyl acetate solution was washed with water (2×300 ml) and brine (2×300 ml), dried over anhydrous magnesium sulfate, filtered and concentrated to a solid.

The solid was purified by flash chromatography over a silica gel column (silica, 170 gm, eluted with a gradient of 1–5% methanol/dichloromethane, 6 L). The fractions containing the desired product were combined and concentrated to give 10.3 gm of solid.

Recrystallization from ethanol (55 ml) and thereafter from ethyl acetate (75 ml) yielded 4.4 g of crystals, m.p. 202°–203° C.

ANALYSIS: Calculated for $C_{22}H_{27}N_3$: 79.23%C, 8.16%H, 12.60%N, Found: 79.50%C 8.19%H, 12.66%N.

EXAMPLE 8

6-(Piperidin-4-yl)-1,2,6,7-tetrahydrobenzo[b]pyrrolo[3,2,1-jk][1,4]benzodiazepine hydrochloride To a 1 L, 3-necked round bottom flask equipped with a reflux condenser, nitrogen inlet, magnetic stirring bar and addition funnel were fed 6-(1-methylpiperidin-4-yl)-1,2,6,7-tetrahydrobenzo[b]pyrrolo[3,2,1-jk][1,4]benzodiazepine (19.3 gm), collidine (622 gm) and dichloromethane (500 ml). The mixture was heated to a gentle reflux and alpha-chloroethyl chloroformate (19 gm) was added dropwise over a period of 30 minutes at refluxing temperature. The resultant solution was refluxed for 2 hours and thereafter cooled to about 50° C. The solution was concentrated to a solid-oil mixture and thereafter extracted with ether (about 2 L). The insolubles were filtered off and the ethereal solution was concentrated and dried on a rotary evaporator (high vacuum pump at about 80° C.) until little collidine was left. The crude product (43 gm) was identified as the bis-alpha-chloroethyl carbamate of the desired product.

The hydrolytic removal of the carbamate groups took place on a flash chromatography column (460 gm of silica, eluted with a gradient of solvents: 1:1 hexane/dichloromethane, 4 L; 1:3 hexane/dichloromethane, 4 L; dichloromethane, 4 L; 1% diethylamine/dichloromethane, 4 L; 2% diethylamine/dichloromethane, 4 L; 2% methanol/2% diethylamine/dichloromethane, 4 L; and finally 15% methanol/5% diethylamine/80% dichloromethane, 4 L). The fractions (15% methanol/5% diethylamine/80% dichloromethane) containing the desired product were concentrated to yield a solid (9.3 gm). Recrystallization twice from ethanol yielded 5.36 gm of crystals, mp>250°.

ANALYSIS: Calculated for $C_{20}H_{23}N_3.HCl$: 70.26%C, 7.08%H, 12.29%N, Found: 69.98%C, 7.17%H, 12.15%N.

EXAMPLE 9

6-(1-Methylpiperidin-4-yl)-1,2,6,7-tetrahydrobenzo[b]pyrrolo[3,2,1-jk][1,4]benzodiazepine-7-carboxylic acid, 2,2,2-trichloroethyl ester To a stirred mixture prepared from 22.7 g of 6-(1-methylpiperidin-4-yl)-1,2,6,7-tetrahydrobenzo[b]pyrrolo[3,2,1-jk][1,4]benzodizepine, 25.2 g of powdered anhydrous sodium bicarbonate and 350 ml of chloroform was added at a rapid drip over 35 minutes under nitrogen a solution prepared from 30 ml of 2,2,2-trichloroethyl chloroformate and 200 ml of chloroform. After an overnight stirring at room temperature, 25 g of sodium bicarbonate and 9.8 ml of 2,2,2-trichloroethyl chloroformate were added, and the reaction was continued for another 2 hours at room temperature. Thereafter, 500 ml of water was added, and the two-phase mixture was stirred for a while and poured into a separatory funnel. The phases were then separated and the chlorform phase was washed with 100 ml of saturated aqueous sodium bicarbonate solution and 100 ml of saturated aqueous sodium chloride solution, and dried over anhydrous sodium sulfate. Filtration and concentration of the filtrate in vacuo afforded an oil, most of which was dissolved in 200 ml of ethyl acetate. Addition of 25 ml of hydrogen chloride-saturated ether followed by 20 ml of ether produced a gum, from which the liquid phase was decanted. This material was allowed to stand overnight in a stoppered flash under 250 ml of ether. Subsequent trituration, filtration and drying afforded crude hydrochloride salt as a solid foam. Suspension of this material in 250 ml of water followed by addition of 350 ml of ethyl acetate and 250 ml of saturated sodium bicarbonate solution to the stirred suspension partitioned all solids between the two liquid phases. The phases were separated and the aqueous phase was extracted with another 150 ml of ethyl acetate. The combined ethyl acetate extracts were washed with 100 ml of saturated sodium bicarbonate solution, 100 ml of water and 100 ml of saturated sodium chloride solution, and dried over anhydrous sodium sulfate. Filtation and concentration of the filtrate in vacuo afforded a solid, which was taken up in 400 ml of boiling cyclohexane and gravity-filtered. After the filtrate had cooled to room temperature, it was gravity-filtered again, and this filtrate was concentrated in vacuo to a solid. Recrystallization of this material from 25 ml of 2-butanone afforded 5.74 g of crystalline solid, m.p. 160°–162° C.

ANALYSIS: Calculated for $C_{24}H_{26}Cl_3N_3O_2$: 58.25%C, 5.30%H, 8.49%N, Found: 58.32%C, 5.32%H, 8.45%N.

EXAMPLE 10

6-[1-(2,2,2-Trichloroethoxycarbonyl)-piperidin-4-yl]-1,2,6,7-tetrahydrobenzo[b]pyrrolo[3,2,1-jk][1,4]benzodiazepine-7-carboxylic acid, 2,2,2-trichloroethyl ester A mixture of 3.43 g of 6-(1-methylpiperidin-4-yl)-1,2,6,7-tetrahydrobenzo[b]pyrrolo[3,2,1-jk][1,4]benzodiazepine-7-carboxylic acid, 2,2,2-trichloroethyl ester, 140 ml of benzene and 4.77 g of milled, anhydrous potassium carbonate was stirred under nitrogen and 1.2 ml of 2,2,2-trichloroethyl chloroformate was added. After an overnight reflux, another 1.2 ml of the chloroformate was added and reflux continued for 1 hour. After further addition of another 1.2 ml of chloroformate and another 1.5 hours of reflux, the mixture was allowed to cool to room temperature and 100 ml of distilled water was added. After short period of stirring, the mixture was poured into a separatory funnel and the phases were separated. The aqueous phase was basic to pH paper. It was extracted with 100 ml of ethyl acetate. The combined organic extracts were washed with 50 ml of 2N aqueous hydrochloric acid solution, 100 ml of saturated sodium bicarbonate solution, 100 ml of water and finally 100 ml of saturated sodium chloride solution and thereafter dried over anhydrous sodium sulfate. Filtration and concentration of the filtrate in vacuo afforded a crude product contaminated with excess reagent. Flash chromatography on 280 g of silica gel using 1:1 dichloromethane/hexane as solvent afforded a gum, which was triturated to solid with 2:1 petroleum ether/ether solution. Filtration, washing and drying afforded 3.07 g of solid, m.p. 202°–205° C.

ANALYSIS: Calculated for $C_{26}H_{25}Cl_6N_3O_4$: 47.59%C, 3.84%H, 6.40%N, Found: 47.20%C, 3.98%H, 6.27%N.

EXAMPLE 11

7-Formyl-6-(1-methylpiperidin-4-yl)-1,2,6,7-tetrahydrobenzo[b]pyrrolo[3,2,1-jk][1,4]benzodiazepine formate A solution of acetic acid (14.1 ml) and formic acid (14.8 ml) was prepared at −10° C. (methanol-ice) over a period of 1.5 hours. This solution, the mixed formic/acetic anhydride reagent, was added to 6-(1-methylpiperidin-4-yl)-1,2,6,7-tetrahydrobenzo[b]pyrrolo[3,2,1-jk][1,4]benzodiazepine (16 gm) at room temperature in one portion. The mixture was stirred for 30 minutes. The resulting solution was treated with methanol (30 ml) and concentrated to an oil.

Purification was effected by flash chromatography over a silica gel column (170 gm, gradient elution with dichloromethane, 2 L; dichloromethane/methanol/diethylamine, 98:1:1%, 2 L; and dichloromethane/methanol/diethylamine, 96:2:2%, 2 L). The fractions containing the pure product were pooled and concentrated to an oil which turned into solid (15.8 gm) upon trituration with ether. A pure sample was prepared from 4 gm of this material by recrystallization from hot methanol (about 5 ml) and ether (20 ml), m.p. 168.5°–170° C.

ANALYSIS: Calculated for $C_{22}H_{25}N_3O.CH_2O_2$: 70.20%C, 6.91%H, 10.67%N, Found: 69.84%C, 6.89%H, 10.56%N.

EXAMPLE 12

7-Methyl-6-(1-methylpiperidin-4-yl)-1,2,6,7-tetrahydrobenzo[b]pyrrolo[3,2,1-jk][1,4]benzodiazepine 7-Formyl-6-(1-methylpiperidin-4-yl)-1,2,6,7-tetrahydrobenzo[b]pyrrolo[3,2,1-jk][1,4]benzodizepine (11.8 gm) was dissolved in tetrahydrofuran (THF, 120 ml) at room temperature. Borane/methyl sulfide complex (2M in THF, 41 ml) was introduced dropwise under nitrogen. The mixture was stirred overnight at room temperature. The reaction mixture was treated slowly with methanol (60 ml) and stirred at 55° C. for 30 minutes. The solution was then concentrated to an oil on a rotary evaporator. Acetic acid (25 ml) and concentrated hydrochloric acid (10 ml) were added and the mixture was refluxed for 25 minutes. The mixture was cooled to room temperature, diluted with methanol (150 ml) and concentrated to about 30 ml. This was treated with water (50 ml), basified with 50% sodium hydroxide solution and extracted with ether (2×350 ml). The ether solution was washed with water (200 ml) and brine (2×300 ml), dried over anhydrous magnesium sulfate and concentrated to dryness. The crude solid (12 gm) was recrystallized from methanol/ether to yield 5.35 g of microcrystalline powder, m.p. 138°–139° C.

ANALYSIS: Calculated for $C_{22}H_{27}N_3$: 79.23%C, 8.16%H, 12.60%N, Found: 78.99%, 8.41%H, 12.87%N.

EXAMPLE 13

4-Bromobenzo[b]pyrrolo[3,2,1-jk][1,4]benzodiazepine

A solution of 2,3-dichloro-5,6-dicyano-1,4-benzoquinone (DDQ, 22 g) in toluene (200 ml) was added dropwise to a refluxing solution of 4-bromo-1,2-dihydrobenzo[b]pyrrolo[3,2,1-jk][1,4]benzodiazepine (10 g) in toluene (750 ml) under nitrogen. The mixture was refluxed for 1 hour, cooled, stirred with triethylamine (3 g) for 10 minutes, and fed to a flash chromatography column (slurry packed with silica, 300 g in dichloromethane). The adsorbed material was eluted with dichloromethane (4 L); 1% methanol/dichloromethane (2 L); and 1% methanol/0.5% ammonium hydroxide/dichloromethane (2 L), whereby the desired product was separated from the remaining quinone. The crude product (10 g) was purified further on a second flash chromatography column (silica gel, 180 g; eluted with 20:80 hexane/dichloromethane, 6 L). The desired product was isolated as a solid (5.4 g). Recrystallization from ethanol (70 ml) at 0° C. gave 3.2 g of crystals which turned to powder after vacuum drying at 110° C., m.p. 122°–123° C.

ANALYSIS: Calculated for $C_{15}H_9BrN_2$: 60.63%C, 3.05%H, 9.34%N, Found: 60.58%C, 2.99%H, 9.38%N.

EXAMPLE 14

N-[2-(2,3-Dihydro-1H-indol-1-yl)phenyl]-4-pyridinecarboxamide

To a solution prepared from N-(2-aminophenyl)indoline hydrochloride (10 gm), triethylamine (15 ml) and chloroform (250 ml) was added isonicotinyl chloride hydrochloride (8 gm) in small portions at 0° C. The mixture was stirred at room temperature for 2 hours. The solvent was removed on a rotary evaporator. The crude residue was loaded on top of a flash chromatography column (silica, 160 gm) and eluted with dichloromlethane (3 L). The fractions containing the pure product were pooled and concentrated to give a solid (9.5 gm). Recrystallization from hot ethanol yielded crystals (7.17 gm), m.p. 120°-121° C.

ANALYSIS: Calculated for $C_{20}H_{17}N_3O$: 76.17%C, 5.43%H, 13.32%N, Found: 76.34%C, 5.19%H, 13.01%N.

EXAMPLE 15

6-(4-Pyridinyl)-1,2-dihydrobenzo[b]pyrrolo[3,2,1-jk][1,4]benzodiazepine

N-[2-(2,3-dihydro-1H-indol-1-yl)phenyl]-4-pyridinecarboxamide (10 gm) in phosphorous oxychloride (300 ml) was refluxed under nitrogen for 4.5 hours. Themixture was cooled to room temperature. The excess of phosphorous oxychloride was removed under reduced pressure (55° C.). The residue was partitioned between dichloromethane and 10% sodium hydroxide solution (600 ml:600 ml). The organic phase was separated and washed with water (250 ml) and brine (2×500 ml). The solution was dried over anhydrous magnesium sulfate and concentrated to about 10 gm of gum. Purification was effected by flash chromatography (silica, 150 gm, eluted with 1.5% methanol/98.5% dichloromethane, 4 L) to yield 6.7 gm of solid. Recrystallization from hot ethanol (70 ml) yielded 5.24 gm of crystals, m.p. 152°-153° C.

ANALYSIS: Calculated for $C_{20}H_{15}N_3$: 80.78%C, 5.09%H, 15.13%N, Found: 80.67%C, 5.19%H, 14.09%N.

EXAMPLE 16

2,3-Dihydro-1H-quino[1,8-ab][1,5]benzodiazepine

To a stirred solution of 32.8 g of N-[2-(1,2,3,4-tetrahydro-1-quinolinyl)phenyl]formamide in 500 ml of dry toluene was added 99.6 g of phosphorus oxychloride. The initial solution was heated under nitrogen for 5 hours at 75° and thereafter stirred at room temperature overnight. The solvent and excess phosphorus oxychloride were removed at aspirator pressure with mild heating. The residue was washed twice with ether and twice with hexane to remove traces of phosphorus oxychloride. The residue was triturated and heated with 25 ml of ethanol. The ethanol was removed on a rotary evaporator and the resulting material was treated with 1 liter of ethyl acetate and 50 ml of dilute sodium hydroxide solution. The two phases were stirred vigorously until the residue was dissolved (except for some interfacial material). The dark aqueous layer was separated and back-extracted with 250 ml of ethyl acetate. The combined organic extracts were filtered, washed four times with water, dried over anhydrous sodium sulfate, and concentrated in vacuo to leave 25.2 g. A part of this material (20 g) was purified further by chromatography on 500 g of silica gel (column packed in dichloromethane) using dichloromethane as eluant. The appropriate fractions were combined and concentrated to afford 9.1 g of crystalline product. This material was recrystallized from a small volume of toluene to provide 4.9 g, m.p. 118°-120° C.

ANALYSIS: Calculated for $C_{16}H_{14}N_2$: 82.02%C, 6.02%H, Found: 82.01%C, 5.91%H.

EXAMPLE 17

7-(1-Methyl-4-piperidinyl)-2,3,7,8-tetrahydro-1H-quino[1,8-ab][1,5]benzodiazepine hemifumarate hemihydrate A stirred mixture of 8.51 g of magnesium turnings in 45 ml of tetrahydrofuran was brought to reflux under nitrogen. To this was added 0.5 ml of 1,2-dibromoethane to initiate a Grignard reaction. The mixture quickly became turbid and there was then added a solution of 46.8 g of 4-chloro-N-methylpiperidine in 70 ml of tetrahydrofuran. About one-quarter of the solution was added in one portion to produce a vigorous Grignard reaction. The rest was added dropwise at such a rate as to sustain reflux without external heating. The total addition time was 0.5 hour and there was produced a milky-white mixture with only a few pieces of magnesium visible. The mixture was refluxed for 1 hour and then cooled to room temperature. To this was added a solution of 16.4 g of 2,3-dihydro-1H-quino[1,8-ab][1,5]benzodiazepine in 100 ml of tetrahydrofuran, dropwise over a 0.5 hour period. After completion of the addition, the mixture was refluxed for 1 hour and thereafter cooled to room temperature. The mixture was quenched into 500 ml of cold saturated ammonium chloride solution with vigorous stirring. There was then added 1 liter of ethyl acetate to extract the product. The layers were separated. The aqueous phase was extracted twice with 250 ml portions of ethyl acetate. The ethyl acetate extracts were combined, washed three times with brine, dried over anhydrous sodium sulfate, and concentrated in vacuo to 23.7 g of waxy crystalline solid. This material was dissolved in 200 ml of ethanol and treated with a warm solution of 9.28 g of fumaric acid in 200 ml of ethanol. After several hours of stirring, the crystalline salt was collected and found to weigh 15.6 g. Recrystallization from 400 ml of ethanol afforded 9.8 g, m.p. 228°-231° C.

ANALYSIS: Calculated for $C_{22}H_{27}N_3.0.5C_4H_4O_4.0.5H_2O$: 72.02%C, 7.63%H, 10.36%N. Found: 71.74%C, 7.53%H, 10.41%N.

We claim:
1. A compound having the formula

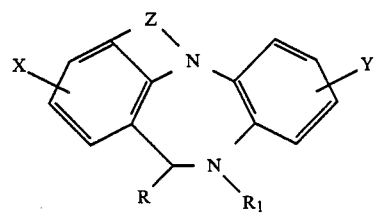

where X is hydrogen, loweralkyl, trifluoromlethyl or halogen; Y is hydrogen, loweralkyl, trifluoromethyl or halogen; Z is —CH₂CH₂—, —CH=CH— or —CH₂CH₂CH₂—; R is

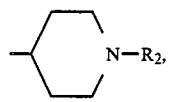

$R_2$ being hydrogen, loweralkyl, ethoxycarbonyl, 2,2,2-trichloroethoxycarbonyl or phenoxycarbonyl; and $R_1$ is hydrogen, loweralkanoyl, loweralkyl, ethoxycarbony, 2,2,2-trichloroethoxycarbonyl or phenoxycarbonyl; or a pharmaceutically acceptable acid addition salt thereof.

2. The compound as defined in claim 1, where Z is —$CH_2CH_2$—.

3. The compound as defined in claim 1, where $R_1$ is hydrogen.

4. The compound as defined in claim 1, where Z is —$CH_2CH_2CH_2$—.

5. The compound as defined in claim 2, where R is

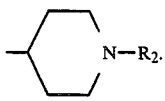

6. The compound as defined in claim 5, which is 6-(1-methylpiperidin-4-yl)-1,2,6,7-tetrahydrobenzo[b]pyrrolo[3,2,1-jk][1,4]benzodiazepine.

7. The compound as defined in claim 5, which is 4-bromo-6-(1-methylpiperidin-4-yl)-1,2,6,7-tetrahydrobenzo[b]pyrrolo[3,2,1-jk][1,4]benzodiazepine.

8. The compound as defined in claim 5, which is 9-bromo-6-(1-methylpiperidin-4-yl)-1,2,6,7-tetrahydrobenzo[b]pyrrolo[3,2,1-jk][1,4]benzodiazepine.

9. The compound as defined in claim 5, which is 4,9-dibromo-6-(1-methylpiperidin-4-yl)-1,2,6,7-tetrahydrobenzo[b]pyrrolo[3,2,1-jk][1,4]benzodiazepine.

10. The compound as defined in claim 5, which is 9-fluoro-6-(1-methylpiperidin-4-yl)-1,2,6,7-tetrahydrobenzo[b]pyrrolo[3,2,1-jk][1,4]benzodiazepine.

11. The compound as defined in claim 5, which is 9-methyl-6-(1-methylpiperidin-4-yl)-1,2,6,7-tetrahydrobenzo[b]pyrrolo[3,2,1-jk][1,4]benzodiazepine.

12. The compound as defined in claim 5, which is 6-(piperidin-4-yl)-1,2,6,7-tetrahydrobenzo[b]pyrrolo[3,2,1-jk][1,4]benzodiazepine.

13. The compound as defined in claim 5, which is 6-(1-methylpiperidin-4-yl)-1,2,6,7-tetrahydrobenzo[b]pyrrolo[3,2,1-jk][1,4]benzodiazepine-7-carboxylic acid, 2,2,2-trichloroethyl ester.

14. The compound as defined in claim 5, which is 6-[1-(2,2,2-trichloroethoxycarbonyl)-piperidin-4-yl]-1,2,6,7-tetrahydrobenzo[b]pyrrolo[3,2,1-jk][1,4]benzodiazepine-7-carboxylic acid, 2,2,2-trichloroethyl ester.

15. The compound as defined in claim 5, which is 7-formyl-6-(1-methylpiperidin-4-yl)-1,2,6,7-tetrahydrobenzo[b]pyrrolo[3,2,1-jk][1,4]benzodiazepine.

16. The compound as defined in claim 5, which is 7-methyl-6-(1-methylpiperidin-4-yl)-1,2,6,7-tetrahydrobenzo[b]pyrrolo[3,2,1-jk][1,4]benzodiazepine.

17. The compound as defined in claim 4, which is 7-(1-methyl-4-piperidinyl)-2,3,7,8-tetrahydro-1H-quino[1,8-ab][1,5]benzodiazepine.

18. A pharmaceutical composition which comprises an effective amount of a compound as defined in claim 1 and a carrier therefor.

19. A method of treating a patient in need of relief from inflammation which comprises administering to the patient an effective inflammation-alleviating amount of a compound as defined in claim 1.

20. A method of treating a patient in need of relief from pain which comprises administering to the patient an effective pain alleviating amount of a compound as defined in claim 1.

* * * * *